United States Patent [19]

Dappen

[11] Patent Number: 4,637,978

[45] Date of Patent: Jan. 20, 1987

[54] ASSAY FOR ANALYSIS OF WHOLE BLOOD

[75] Inventor: Glen M. Dappen, Webster, N.Y.

[73] Assignee: Eastman Kodak Company, Rochester, N.Y.

[21] Appl. No.: 546,694

[22] Filed: Oct. 28, 1983

[51] Int. Cl.[4] .......................... C12Q 1/60; C12Q 1/54; C12Q 1/26; C12Q 1/28

[52] U.S. Cl. ....................................... 435/11; 435/14; 435/25; 435/28; 435/805; 436/169; 436/170; 436/810; 422/56; 422/57

[58] Field of Search ....................... 435/11, 10, 14, 28, 435/25, 805; 422/56, 57; 436/169, 170, 810

[56] References Cited

U.S. PATENT DOCUMENTS

| | | | |
|---|---|---|---|
| 3,983,005 | 9/1976 | Goodhue et al. | 435/19 |
| 3,992,158 | 11/1976 | Przybylowicz et al. | 435/14 |
| 4,042,335 | 8/1977 | Clément. | |
| 4,098,574 | 7/1978 | Dappen. | |
| 4,144,306 | 3/1979 | Figueras. | |
| 4,258,001 | 3/1981 | Pierce et al. | |
| 4,292,272 | 9/1981 | Kitajima et al. | |
| 4,312,834 | 1/1982 | Vogel et al. | |
| 4,384,042 | 5/1983 | Miike et al. | 435/25 |

FOREIGN PATENT DOCUMENTS

| | | |
|---|---|---|
| 3150102 | 7/1982 | Fed. Rep. of Germany. |
| 57-101760 | 6/1982 | Japan. |
| 911181 | 11/1962 | United Kingdom. |

*Primary Examiner*—Esther M. Kepplinger
*Attorney, Agent, or Firm*—J. Lanny Tucker

[57] ABSTRACT

Disclosed herein is an assay useful for the determination of an analyte in whole blood. In particular, this assay is useful for the quantitative determination of peroxide-generating analytes, such as glucose or cholesterol, in whole blood. This assay utilizes a multizone element consisting essentially of a support having thereon, in order and in fluid contact, a registration zone and a reagent/spreading zone. The reagent/spreading zone has a void volume and average pore size effective to accommodate whole blood, and contains an interactive composition necessary for the analysis. Such composition is capable of providing, upon interaction with the analyte, a dye which can be spectrophotometrically detected at a wavelength greater than about 600 nm.

30 Claims, 6 Drawing Figures

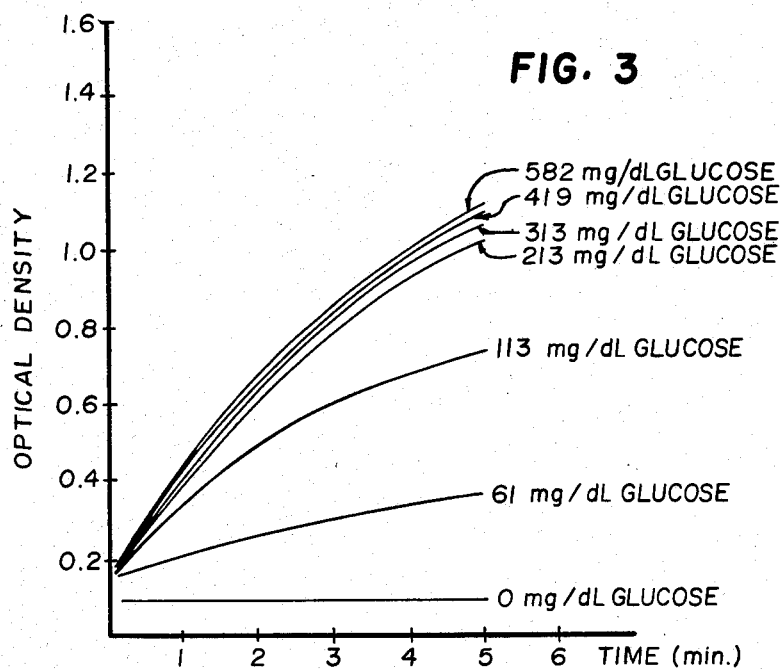
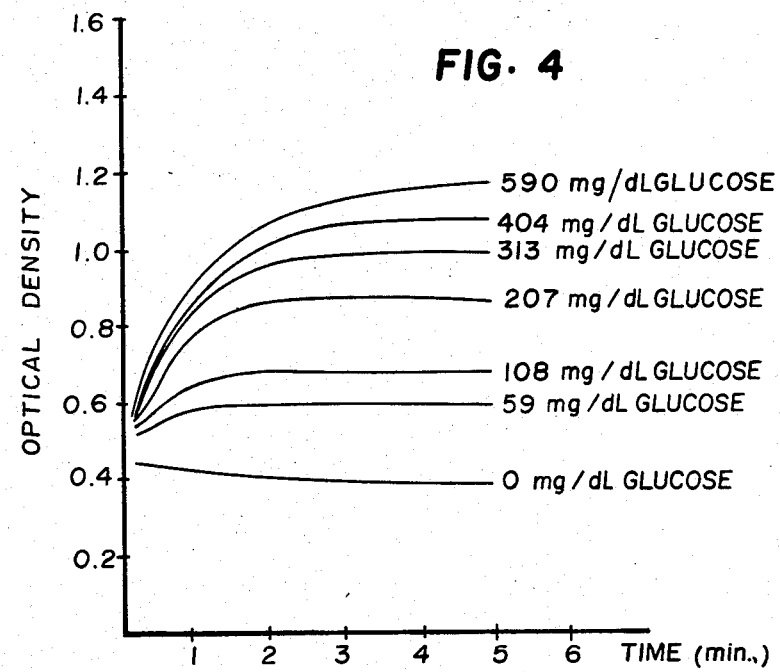

ASSAY FOR ANALYSIS OF WHOLE BLOOD

FIELD OF THE INVENTION

The present invention relates to a "dry chemistry" assay for whole blood. In particular, it relates to an assay useful for the quantitative determination of peroxide-generating analytes, e.g. glucose or cholesterol, in whole blood. This invention also relates to multizone elements useful in such an assay.

BACKGROUND OF THE INVENTION

In order to provide desired preventative or diagnostic health care, a physician must often determine the level of various analytes in a patient's blood. For example, the level of glucose or cholesterol in the blood is often important in effective treatment of various diseases, e.g. diabetes, hypoglycemia, liver and thyroid disorders and atherosclerosis.

Generally, such analytes are measured in blood serum or plasma after the whole red blood cells have been removed. However, it would be desirable to be able to measure analytes in undiluted whole blood, thereby avoiding procedures required for separating red blood cells from the rest of the fluid and attendant labor and equipment costs. Using undiluted whole blood in analyses would also allow for simpler and faster sample procurement and processing. This would be especially useful for home monitoring assays wherein the assay procedure should be as simple as possible.

"Dry chemistry" assays are known. Such assays are analytical clinical techniques wherein chemical reagents are incorporated in various substantially "dry-to-the-touch" elements, e.g. test strips and multizone analytical elements. The advantages of "dry chemistry" assays over "wet chemistry" assays (i.e. techniques using reagents in solutions) are also known and include simplicity of use, economic savings and rapid analysis. However, analysis of whole blood using dry chemistry assays must overcome a serious problem. The corpuscular (red and white cells) and other high molecular weight components of whole blood must either be removed from the sample or somehow accommodated by the element in order to provide an accurate assay. State-of-the-art dry assays require removal of corpuscular components by allowing serum or plasma to penetrate an element and wiping off the corpuscular components which are unable to penetrate. Alternatively, for an element to accommodate the components, the void volume and pore size within the surface contacted by a blood sample must be sufficient to completely absorb the sample without clogging the analytical element. At the same time, the pore structure must not be so large as to cause mechanical instability (i.e. disintegration or fragmentation) of the element.

This problem is recognized in U.S. Pat. No. 4,312,834 (issued Jan. 26, 1982 to Vogel et al) wherein a monolayer diagnostic agent for analysis of fluids is disclosed. This diagnostic agent comprises a film forming material having a film opener therein to provide porosity. When the diagnostic agent is to be used for the detection of high molecular weight and corpuscular materials, the ratio of film opener to film former is higher than when low molecular weight materials are to be detected. However, the diagnostic agent taught by this reference has insufficient porosity to absorb whole blood cells as seen in Examples 4 and 5 wherein residual blood was wiped off the agent after 1 minute reaction time and prior to spectrophotometric measurement. The practice of wiping off residual corpuscular components prior to quantitative measurement of an analyte is common to commercially-available whole blood elements or diagnostic agents (see, e.g. U.K. No. 911,181, published Nov. 21, 1962).

Whole blood can also be assayed with an element which has a porous outer spreading layer which acts as a filter to trap the large corpuscular components of whole blood while allowing the serum or plasma to pass through to a separate reagent layer, which layer contains the necessary reagents for causing a detectable change to occur in the presence of a particular analyte. This technique is illustrated, for example, in Column 25 of U.S. Pat. No. 4,144,306 (issued Mar. 13, 1979 to Figueras), Example 4 of U.S. Pat. No. 4,258,001 (issued Mar. 24, 1981 to Pierce et al), Example 3 of U.S. Pat. No. 4,292,272 (issued Sept. 29, 1981 to Kitajima et al) and Example 2 of Japanese Patent Publication No. 57-101760 (published June 24, 1982).

However, it would be advantageous to avoid the need to separate the serum or plasma from corpuscular components in whole blood. This procedure of filtering the components from the serum or plasma using a filter layer is a slow process. There is also the likelihood that a portion of the analyte is lost in the filter/spreading layer as the plasma or serum passes through it, thereby resulting in an inaccurate analysis.

U.S. Pat. No. 4,042,335 (issued Aug. 16, 1977 to Clement) describes a whole blood assay utilizing a multilayer analytical element. The described whole blood element comprises a support having thereon, in order, a registration layer, a radiation-blocking layer and a reagent layer. The reagent layer can act as a porous spreading layer while the radiation-blocking layer can act as a filter layer to filter out and exclude whole blood cells from the registration layer (see FIG. 1 of the reference), thereby avoiding interference by hemoglobin.

While such an element may be used to determine an analyte in whole blood, its usefulness depends to a large degree on having a detectable species which can rapidly diffuse through the radiation-blocking layer to the registration layer and which has a sufficiently high extinction coefficient. However, not all detectable species (e.g. dyes, color-forming couplers, etc.) satisfy these requirements.

Hence, it would be desirable to have a simple and rapid "dry chemistry" assay for undiluted whole blood which provides rapid and accurate analysis and eliminates the need to wipe off residual blood.

SUMMARY OF THE INVENTION

The present invention provides a "dry chemistry" assay useful for determination of an analyte in undiluted whole blood. This assay overcomes the problems associated with known whole blood assays. Namely, it is simple, rapid, accurate and can be used to analyze undiluted whole blood samples. The assay of this invention obviates the need to wipe off excess blood (i.e. corpuscular components) or to dilute the blood sample. Further, it makes separation of the cellular components of the blood from the plasma or serum unnecessary, and eliminates the need for separate radiation-blocking/filter layers. Interference by hemoglobin is not a concern with the assay of this invention because the dye provided in the interaction with the analyte is spectrophotometrically detectable at a wavelength greater than about 600 nm. Surprisingly, the assay of this invention is also extremely rapid, i.e. it generally provides analysis in 2 or 3 minutes or less. Another unexpected advantage provided by this assay is its insensitivity to fluctuations in hematocrit and hemoglobin values from sample to sample.

Therefore, in accordance with this invention, a method for the determination of an analyte in whole blood comprises the steps of:

(A) physically contacting a sample of whole blood and a multizone element, which element consists essentially of a support having thereon, in order and in fluid contact, a registration zone and a reagent/spreading zone, the reagent/spreading zone having a void volume and average pore size effective to accommodate whole blood, and containing an interactive composition capable of providing, upon interaction with the analyte, a dye which can be spectrophotometrically detected at a wavelength greater than about 600 nm; and (B) detecting such dye at a wavelength greater than about 600 nm.

BRIEF DESCRIPTION OF THE DRAWINGS

FIGS. 2 and 3 are graphical plots of reflectance density measured at 565 nm vs. time (min.) for assays of undiluted whole blood samples containing various amounts of glucose determined according to the teaching of the prior art.

FIG. 4 is a graphical plot similar to FIG. 1 except that the glucose assay was carried out using another color-forming coupler.

DETAILED DESCRIPTION OF THE INVENTION

Figure 1:
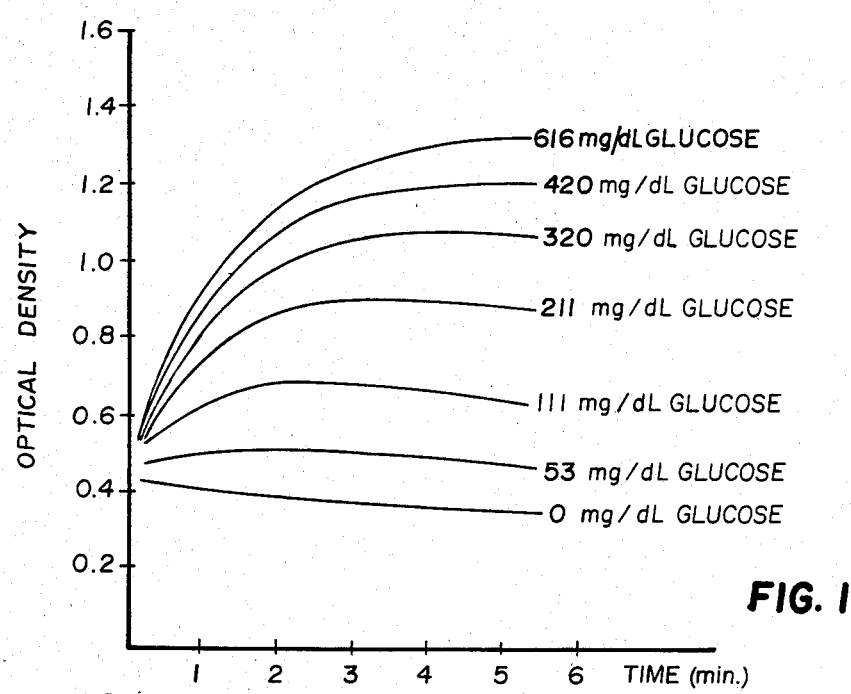
FIG. 1 is a graphical plot of reflectance density measured at 660 nm vs. time (min.) for assays of undiluted whole blood samples containing various amounts of glucose determined according to this invention.

The assay of this invention is useful for the quantitative determination of an analyte in whole blood. For example, the assay of this invention can also be used as an immunoassay with a particular antigen considered the analyte to be determined. This assay is particularly useful for determining peroxide-generating analytes, such as glucose, cholesterol, uric acid, glycerol, triglycerides, etc. Preferably, this invention is used for quantitative analysis of glucose or cholesterol, and most preferably, of glucose.

The assay of this invention is suitable for analysis of whole blood, diluted or undiluted. But one of its advantages is its capability for analyzing undiluted whole blood. By "undiluted" whole blood is meant whole blood which has not been thinned with saline solution, serum, plasma, etc. The advantages obtained with the assay of this invention are possible with the use of a multizone element which has two essential zones, a spreading/reagent zone which can accommodate, or absorb, a whole blood sample (e.g. 5-20 μL) without the need to wipe off excess blood, and a registration zone to which dye formed in response to the presence of an analyte migrates.

Generally, in order to accommodate an undiluted whole blood sample, the void volume in the reagent/spreading layer is in the range of from about 25 to about 80 percent depending upon the materials used, and preferably from about 40 to about 60 percent. The average pore size is generally at least 5 microns, and more likely from about 15 to about 65 microns depending upon the materials used.

The reagent/spreading zone can be prepared from any suitable fibrous or non-fibrous material or mixtures thereof as long as the zone can accommodate whole blood with the appropriate void volume and average pore size. The reagent/spreading zone advantageously produces a uniform concentration of whole blood per unit area at its surface facing the registration zone with which the reagent/spreading zone is in fluid contact. Such uniformity of concentration can be determined by densitometric or other analytical techniques known in the art.

Useful reagent/spreading zones can be prepared using fibrous materials, either mixed with a suitable binder material or woven into a fabric, as described in U.S. Pat. No. 4,292,272 (issued Sept. 29, 1981 to Kitajima et al), the disclosure of which is incorporated herein by reference in its entirety. Alternatively, the zones are isotropically porous and can be prepared using polymeric compositions (e.g. blush polymers), according to the teaching of U.S. Pat. No. 3,992,158 (issued Nov. 16, 1976 to Przybylowicz et al), the disclosure of which is incorporated herein by reference in its entirety.

Isotropically porous reagent/spreading zones can also be prepared with particulate material wherein the isotropic porosity is created by interconnected spaces between the particles. Various types of particulate matter, all desirably non-swellable in and chemically inert and impermeable to whole blood components, are useful including, for example, pigments (e.g. titanium dioxide, barium sulfate, etc.), diatomaceous earth, colloidal materials (e.g. microcrystalline cellulose), resinous or glass beads and the like. If a particulate material of choice is not adherent, it can be treated to obtain particles that adhere to each other on surface areas of adjacent particles where those particles are in closest proximity to form a coherent, three-dimensional lattice which is non-swellable in whole blood.

Examples of other useful particulate materials include the polymer particles described in W. German OLS No. 3,150,102 (published July 29, 1982 and assigned to Konishiroku Photo), which particles are chemically bonded through reactive groups at the points of particle contact which reactive groups are incorporated in the particles; and the polymer particles described in Japanese Patent Publication No. 57(1982)-101760 (published June 24, 1982 and assigned to Konishiroku Photo), which particles are chemically bonded at points of contact with a low molecular weight adhesive compound (e.g. reaction products of bisphenols, dicarboxylic acids, and/or amino compounds, etc.).

Particularly useful reagent/spreading zones are those having a particulate structure formed by organo-polymeric particles and polymeric adhesive for those particles described in U.S. Pat. No. 4,258,001 (issued Mar. 24, 1981 to Pierce et al), the disclosure of which is incorporated herein in its entirety. The interconnected voids among the adjacent particles of such a structure accommodate the corpuscular and high molecular weight components of whole blood and provide for transport of analytes therein. Maintaining particulate integrity of the organo-polymeric particles in the particulate structure with a polymeric adhesive prevents the coalescence and flow of these materials into the voids, and the concentration of such adhesive at those particle surface areas of the structure which are contiguous to adjacent particles insures that the adhesive does not flow into and clog the voids.

The materials used to prepare the reagent/spreading zone preferred in the practice of this invention are described in considerable detail in the Pierce et al patent. Since the details and definitions of the reagent/spreading zone are provided in that reference, the present disclosure is directed to a general description of the zone while noting preferred embodiments of this invention. The thickness of the described particulate structure can be widely varied depending upon the size of the organo-polymeric particles and the specific analyte to be determined. However, the thickness is generally within the range of from about 10 to about 500 microns.

The heat-stable, organo-polymeric particles useful in the practice of this invention are generally spherical beads having a particle size in the range of from about 1 to about 200 microns. Preferably, they have a substantially uniform size within the range of from about 20 to about 80 microns.

The particles can be composed of a wide variety of organic polymers, including both natural and synthetic polymers, having the requisite properties. Preferably, however, they are composed of one or more addition polymers formed from one or more ethylenically unsaturated polymerizable monomers, such as addition homopolymers of single monomers or copolymers formed from two or more of such monomers. These polymers can be prepared by any of a variety of conventional polymerization methods (e.g. solution, emulsion, dispersion, suspension, etc.). If desired, although the invention is not so limited, the particular polymer can contain one or more reaction sites to link various interactive compositions to the particles.

Particularly useful addition polymers are those formed by polymerizing one or more of the following ethylenically unsaturated polymerizable monomers, the details of which are provided in the Pierce et al patent noted hereinabove:

(a) from 0 to 100, preferably from 0 to about 99, weight percent of one or more amino-substituent-free vinyl carbocyclic aromatic monomers, including the styrene monomers described in the Pierce et al patent, as well as similar amino-substituent-free vinyl naphthyl monomers;

(b) from 0 to about 25 weight percent of one or more acrylic acid esters;

(c) from 0 to 100, preferably 0 to about 75, weight percent of one or more methacrylic acid esters;

(d) from 0 to about 30 weight percent of one or more ethylenically unsaturated carboxylic acids;

(e) from 0 to about 75 weight percent of one or more ethylenically unsaturated nitrile;

(f) from 0 to about 20 weight percent of one or more amino-substituted vinyl carbocyclic aromatics, including the styrene monomers described in the Pierce et al patent, as well as similar amino-substituted vinyl naphthyls;

(g) from 0 to about 20, preferably 0 to about 10, weight percent of one or more ethylenically unsaturated crosslinkable monomers, including those which can be crosslinked with amines or gelatin hardeners and those having two or more ethylenically unsaturated polymerizable groups;

(h) from 0 to about 20 weight percent of one or more tertiary aminoalkyl acrylates or methacrylates;

(i) from 0 to 100, preferably 0 to about 75, weight percent of one or more polymerizable, N-heterocyclic vinyl monomers; and (j) from 0 to about 20 weight percent of one or more acrylamides or methacrylamides.

Particularly useful addition polymers include those listed in Table I of the Pierce et al patent. The numbers in the brackets represent the weight ratio of monomers in the monomer blend used to prepare the polymer. Poly(vinyltoluene-co-p-t-butyl-styrene-co-methacrylic acid) [61:37:2] is a preferred polymer. The organo-polymeric particles can contain other addenda, if desired, as known in the art.

The polymeric adhesive which is useful in this invention bonds the organo-polymeric particles to one another to provide a coherent, three-dimensional lattice in the reagent/spreading zone. The details of this adhesive are provided in the Pierce et al patent, noted hereinabove. Generally, the adhesive is composed of an organic polymer different from the specific polymer contained in the particles, although quite commonly the adhesive represents a polymer containing many repeating units which are identical or similar to some of those present in the polymer composition of the particles.

Preferably, the adhesive is composed of one or more addition polymers formed from one or more ethylenically unsaturated polymerizable monomers, such as addition copolymers formed from two or more of such monomers. Like the particles, the adhesive can be prepared by any of a variety of conventional polymerization methods.

Generally, the amount of adhesive contained in the particulate structure is less than about 10 percent, and preferably from about 1 to about 5 percent, based on the weight of the particles.

Particularly useful addition polymers employed as adhesives are formed by polymerizing a blend of ethylenically unsaturated polymerizable monomers selected from the blends described as follows, the details of which are provided in the Pierce et al patent noted hereinabove:

A. a blend containing from about 1 to about 35, preferably from about 10 to about 30, weight percent of one or more amino-substituent-free vinyl carbocyclic aromatics as described hereinabove, and from about 65 to about 99, preferably from about 70 to about 90, weight percent of one or more alkyl acrylates or methacrylates;

B. a blend containing from about 20 to about 95, preferably from about 50 to about 95, weight percent of one or more amino-substituent-free vinyl carbocyclic aromatics, acrylic or methacrylic acid esters and ethylenically unsaturated polymerizable crosslinkable monomers, and from about 5 to about 80, preferably from about 5 to about 50, weight percent of one or more ethylenically unsaturated polymerizable monomers having an active hydrogen or salts thereof; and C. a blend containing from about 15 to 100 weight percent of one or more ethylenically unsaturated monomers selected from the group consisting of 1-vinylimidazole, vinylbenzyl alcohol, ethyl acrylate or an acrylamide or methacrylamide, and from 0 to about 85 weight percent of one or more ethylenically unsaturated polymerizable crosslinkable monomers.

Particularly useful addition polymers include those listed in Table II of the Pierce et al patent. The numbers in the brackets represent the weight ratio of monomers in the monomer blend used to prepare the polymer. Poly(n-butyl acrylate-co- styrene-co-2-acrylamido-2-methylpropane sulfonic acid) [70:20:10] is a preferred adhesive polymer.

Generally, the adhesive polymers have a glass transition temperature (Tg) which is at least 20° C., and preferably at least 30° C., less than the Tg of the organopolymer in the particles. Preferred adhesives have a Tg below about 80° C., and generally less than about 30° C. (as measured under high relative humidity conditions, i.e. ≧80% R.H.). The term glass transition temperature is defined herein to be that temperature at which the polymer changes from a glassy polymer to a rubbery or flowable polymer. The Tg can be measured in any suitable manner as described, for example, in "Techniques and Methods of Polymer Evaluation," Vol. 1, Marcel Dekker, Inc., N.Y. (1966).

Various methods can be employed for preparing the particulate structure with the above-described particles and adhesive. Specific details of useful methods are provided in the Pierce et al patent noted hereinabove.

The reagent/spreading zone of the described elements contains one or more interactive compositions. These compositions comprise one or more active components which undergo interaction with an analyte, or a reaction or decomposition product of the analyte, or with each other upon physical contact of a sample of whole blood containing the analyte with the reagent/spreading zone. It is essential to the assay of this invention that such interaction provides a dye which can be spectrophotometrically detected at a wavelength greater than about 600 nm, and preferably greater than about 630 nm. That is, such a dye must have a high enough extinction so that significant optical density can be observed at a wavelength above about 600 nm, and preferably above about 630 nm. The dye can be provided either by interaction with a dye-providing material, or by dye release from a preformed dye. The term "interaction" is meant to refer to chemical activity, catalytic activity as in the formation of an enzyme-substrate complex, immunogenic activity as in an antigen-antibody reaction, and any other form of electrical, chemical or physical interaction that can release, produce or otherwise provide the detectable dye, the concentration of which is directly or indirectly indicative of the presence or concentration of a particular analyte.

Although not essential, the interactive composition can be immobilized in the particulate structure of the reagent/spreading zone to minimize or prevent undesired migration of the composition within the structure or other zones of the element. Immobilization can be accomplished by any suitable technique known to one of ordinary skill in the art.

Particular interactive compositions that can be distributed within the reagent/spreading zone depend upon the assay of choice. Particularly useful interactive compositions comprise a substance having peroxidative activity (defined hereinbelow). In the case of many analyses, enzymes, such as oxidase materials like glucose oxidase or cholesterol oxidase, can desirably be included within the reagent/spreading zone for the analysis of the analyte that is a substrate for such enzyme.

Generally, the interactive composition also includes a dye providing composition. Such compositions include a compound that, when oxidized, can couple within itself or with its reduced form to provide a dye. Such autocoupling compounds include a variety of hydroxylated compounds, such as o-aminophenols, 4-alkoxynaphthols, 4-amino-5-pyrazolones, cresols, pyrogallol, guaiacol, orcinol, catechol, chloroglucinol, p-dihydroxydiphenylgallic acid, pyrocatechoic acid, and salicylic acid. Compounds of this type are well known and described in the literature, such as in *The Theory of the Photographic Process,* Mees and James, 3rd Edition, 1966, especially in Chapter 17.

As another example, the dye can be provided by oxidation of a leuco dye compound. Representative leuco dyes include such substances as triarylimidazole leuco dyes and other leuco dyes, as described in U.S. Pat. No. 4,089,747 (issued May 16, 1978 to Bruschi) and triarylmethane leuco dyes as known in the art.

As yet another example, the dye is formed by dye-providing compositions that include the condensation products of oxidizable compounds with couplers. Representative oxidizable compounds include benzidine and its homologs, p-phenyldiamines, p-aminophenols, an aminoantipyrine, e.g. 4-aminoantipyrine, and the like. A wide range of such couplers including a number of autocoupling compounds, is described in the literature, such as in Mees and James, supra, and in Kosar, *Light Sensitive Systems,* 1965, pages 215–249.

The dye is generally diffusible so that it can move into the permeable registration zone from the reagent/spreading zone.

In a preferred embodiment of the assay of this invention, the reagent/spreading zone comprises an interactive composition necessary for the quantifiable detection of glucose in whole blood. Basically, this interactive composition comprises glucose oxidase which interacts with the analyte glucose, a peroxidative substance (e.g. peroxidase or others known in the art), an aminoantipyrine oxidizable compound (e.g. 4-aminoantipyrine), a suitable buffer which provides a pH in the range of from about 4 to about 7 under conditions of use (i.e. when spotted with a whole blood sample), and a coupler which will react with the aminoantipyrine in its oxidized state. These reagents are well known in the art, as described for example, in U.S. Pat. No. 4,098,574 (issued July 4, 1978 to myself). Any of a number of couplers (e.g. phenols, naphthols, substituted anilines, etc.) can be used in the practice of this invention as long as they, with a suitable oxidizable compound, can provide a dye detectable at a wavelength greater than about 600 nm, and preferabaly greater than about 630 nm.

Useful couplers for the glucose assay of this invention include toluidine compounds including, for example, those described in Japanese Pat. Publication No. 83-22200 (published May 7, 1983); European Patent Application No. 68,356 (published Jan. 5, 1983); U.K. Pat. No. 2,107,863 (published Oct. 22, 1981); and Japanese Patent Publication No. 58-898 (published Jan. 6, 1983). Examples of such useful toluidine compounds include: N-ethyl-N-2-sulfoethyl-m-toluidine, N-ethyl-N-2-carboxyethyl-m-toluidine, N-2-carboxyethyl-m-toluidine, N-sulfomethyl-p-toluidine, N-methyl-N-(2,3-dihydroxypropyl)-m-toluidine, and the like.

Other useful couplers include substituted aniline compounds such as 8-anilino-1-naphthalenesulfonic acid and N-methyl-N-sulfopropylaniline, 1,7-dihydroxynaphthalene and others known in the art.

Similarly, in another embodiment of this invention, a cholesterol assay utilizes a reagent/spreading zone containing cholesterol oxidase which interacts with the analyte cholesterol, cholesterol ester hydrolase, a peroxidative substance (e.g. peroxidase or others known in the art), an aminoantipyrine oxidizable compound (e.g. 4-aminoantipyrine), a suitable buffer which provides a pH in the range of from about 4 to about 7 under conditions of use, and a suitable coupler (e.g. a toluidine or a substituted aniline or others noted hereinabove).

The dry analytical elements of this invention have only two essential zones, namely a reagent/spreading zone containing the interactive composition described hereinabove and a registration zone for receiving the dye resulting from interaction of the interactive composition with the analyte. These zones can be self-supporting (i.e. having integrity), but preferably they are carried on a suitable support. Such a support can be any suitable dimensionally stable, and preferably, transparent (i.e. radiation transmissive) material which transmits electromagnetic radiation of a wavelength between about 200 and about 900 nm. A support of choice for a particular element should be compatible with the intended mode of detection (reflection, fluorescence, or transmission spectroscopy). Useful support materials include polystyrene, polyesters (e.g. poly(ethylene terephthalate)), polycarbonates, cellulose esters (e.g. cellulose acetate), etc. Preferably, the registration zone is immediately adjacent the support although an optional subbing zone can be interposed, if desired. The zones of the element are in fluid contact with each other, meaning that fluids and reagents and reaction products in the fluids can pass between superposed regions of adjacent zones. Stated in another manner, fluid contact refers to the ability to transport components of a fluid between the zones in fluid contact. Preferably, the zones are separate coated layers, although one or more zones can be in a single layer of an element.

The registration zone of the elements receives reaction products formed or released in the reagent/spreading zone. The components of such zones are well known as described in, for example, the patents noted hereinbelow with regard to element configurations and materials in general. Generally, the registration zone contains a hydrophilic binder material, such as gelatin; a hardener, if desired; and a surfactant.

The elements of this invention can also optionally include additional nonessential zones having specialized functions, e.g. making element manufacture more convenient. For example, it is common practice to use additional zones to promote or control adhesion between other zones. Such zones are commonly referred to as "binder" zones or "subbing" zones and are well known in the art. Such subbing zones generally contain one or more naturally-occurring or synthetic polymeric materials including gelatin or other naturally-occurring colloids; or homopolymers and copolymers, such as poly(acrylamide), poly(vinyl pyrrolidone), poly(n-isopropylacrylamide), poly(acrylamide-co-N-vinyl-2-pyrrolidone) and similar copolymers.

An advantage of the assay of this invention, however, is that the elements used therein do not have a radiation-blocking zone or layer, also known sometimes as a reflective zone or layer. Such zones tend to slow down the diffusion of or retain many dyes, and hence make the assay slower or less accurate. Some dyes will not diffuse through this zone at all. For example, the dye formed in an element for determining glucose containing an aminoantipyrine and 8-anilino-1-naphthalenesulfonic acid will not diffuse through a radiation-blocking zone to an appreciable extent. Hence, the assay and element of this invention have distinct advantages by overcoming this problem.

The coverage of each component or reagent in the interactive composition described hereinabove can be widely varied depending upon the analyte to be determined. These coverages are well within the skill of the worker in the art. For example, in an element designed to assay glucose in whole blood, glucose oxidase is generally present in a coverage of up to about 40,000, and preferably from about 20,000 to about 30,000, $U/m^2$. The peroxidative substance (e.g. peroxidase) is generally present in a coverage of up to about 40,000, and preferably from about 20,000 to about 30,000, $U/m^2$. The aminoantipyrine oxidizable compound is generally present in a coverage of up to about 2, and preferably from about 0.3 to about 1.5, $g/m^2$. A buffer (e.g. 3,3-dimethylglutaric acid) is generally present in a coverage of up to about 20, and preferably from about 1 to about 10, $g/m^2$. A coupler to react with the aminoantipyrine (e.g. a toluidine or 8-anilino-1-naphthalenesulfonic acid) is generally present in a coverage of up to about 5, and preferably from about 0.5 to about 2 $g/m^2$.

One or more zones (or layers) of the elements of this invention can contain a variety of one or more other desirable, but optional components, including surfactants, thickeners, enzyme activators, coupler solvents, buffers, binders, hardeners, etc. These components can be present in amounts known to one skilled in the art. Representative element components are described, for example, in U.S. Pat. Nos. 4,258,001; 3,992,158; 4,042,335; 4,144,306, all noted hereinabove; 4,132,528 (issued Jan. 2, 1979 to Eikenberry et al); 4,050,898 (issued Sept. 27, 1977 to Goffe et al); and 4,275,152 (issued June 23, 1981 to Esders et al), the disclosures of which are incorporated herein by reference.

A variety of different elements, depending on the method of assay, can be prepared in accordance with the present invention. Elements can be configured in a variety of forms, including elongated tapes of any desired width, sheets or smaller chips.

The assay of this invention can be manual or automated. In general, the amount of analyte in whole blood is determined by taking the element from a supply roll, chip packet or other source and physically contacting it with a sample of the whole blood. Such contact can be accomplished in any suitable manner, e.g. dipping or immersing the element into the sample or, preferably, by spotting the reagent/spreading zone of the element by hand or machine with a drop of the sample by pipette or other suitable dispensing means.

After sample application, the element is exposed to any conditioning, such as incubation, heating or the like, that may be desirable to quicken or otherwise facilitate obtaining any test result.

The analyte, if present, then interacts with the interactive composition at a rate based on the concentration of analyte in the sample and the rate of formation of the dye is determined. Alternatively, in an end-point assay, the amount of dye formed in direct proportion to the analyte concentration is determined by passing the element through a zone in which suitable apparatus for detecting the dye is provided. For example, the dye can be detected with suitable spectrophotometric apparatus and procedures known in the art.

In the following examples, Zonyl FSN ™ was obtained from DuPont (Wilmington, Delaware), peroxidase was purchased from Miles Laboratories (Elkhart, Indiana), glucose oxidase was obtained from Sigma Corp. (St. Louis, Missouri), cholesterol ester hydrolase was purchased from Enzyme Development Corp. (New York, N. Y.) and cholesterol oxidase was purchased from Upjohn Corp. (Kalamazoo, Michigan). All other reagents and materials were obtained from Eastman Kodak Company (Rochester, New York).

The following examples are provided to illustrate the practice of the present invention:

EXAMPLE 1

Glucose Assay of this Invention and Comparison to Prior Art Assays

This is a comparative example comparing an assay of this invention for determining glucose to prior art glucose assays.

An analytical element for the quantitative determination of glucose in undiluted whole blood was prepared according to this invention in the following manner. On a poly(ethylene terephthalate) film support were coated, in order, a registration layer and a reagent/spreading layer having the component materials listed below.

| Reagent/Spreading Layer | | |
|---|---|---|
| Particulate structure composed of: | | |
| 40–60μ poly(vinyltoluene-co-p-t-butylstyrene-co-methacrylic acid) [61:37:2 weight ratio] beads, and | 100–300 | g/m² |
| poly(n-butyl acrylate-co-styrene-co-2-acrylamido-2-methylpropane sulfonic acid) [70:20:10 weight ratio] adhesive | 2–10 | g/m² |
| Zonyl FSN ™ nonionic fluoro surfactant | 0.5–2 | g/m² |
| Xanthan gum thickener | 0.05–0.5 | g/m² |
| 5,5-Dimethyl-1,3-cyclohexanedione | 0.1–0.5 | g/m² |
| 3,3-Dimethylglutaric acid (pH 5) | 1–10 | g/m² |
| 4-Aminoantipyrine | 0.3–1.5 | g/m² |
| 8-Anilino-1-naphthalenesulfonic acid | 0.5–2 | g/m² |
| Peroxidase | 20,000–30,000 | U/m² |
| Glucose oxidase | 20,000–30,000 | U/m² |
| Registration Layer | | |

| -continued | | |
|---|---|---|
| Gelatin | 5–20 | g/m² |
| Zonyl FSN ™ | 0.05–0.5 | g/m² |
| Bis(vinylsulfonylmethyl)ether hardener | 0.05–0.5 | g/m² |
| Support | | |

Each of several samples of this analytical element was spotted with 10 μL samples of undiluted whole blood containing varied amounts of glucose (0–600 mg/dL). Each element sample was incubated at room temperature for up to 5 minutes, and reflectance density readings were taken at 660 nm at various times within the incubation period using a conventional spectrophotometer.

The results of the spectrophotometric readings, provided in FIG. 1, illustrate excellent differentiation between glucose concentrations and rapid analysis (i.e. within about 2 to 3 minutes) with the assay of this invention.

The prior art assays evaluated in this example utilized the analytical elements described hereinbelow which are labeled Controls A and B.

| | | Control A | Control B | |
|---|---|---|---|---|
| Spreading Layer | Particulate structure same as in above element | | | |
| | Xanthan gum thickener | 0.05–0.5 | 0.05–0.5 | g/m² |
| | Zonyl FSN ™ surfactant | 0.5–2 | 0.5–2 | g/m² |
| Radiation Blocking/ Filter Layer | Titanium Dioxide | 5–15 | 5–15 | g/m² |
| | Gelatin | 0.5–2 | 0.5–2 | g/m² |
| | Bis(vinylsulfonylmethyl)ether hardener | 0.01–1 | 0.01–1 | g/m² |
| | Zonyl FSN ™ surfactant | 0.01–1 | 0.01–1 | g/m² |
| Reagent Layer | Gelatin | 5–20 | 5–20 | g/m² |
| | Bis(vinylsulfonylmethyl)ether hardener | 0.05–0.5 | 0.05–0.5 | g/m² |
| | Zonyl FSN ™ surfactant | 0.05–0.5 | 0.05–0.5 | g/m² |
| | 3,3-Dimethyl glutaric acid (pH 5) | 1–10 | 1–10 | g/m² |
| | 3-Hydroxy-2,4,6-triiodobenzoic acid | 0.5–2 | 0 | g/m² |
| | N—ethyl-N—2-sulfoethyl-m-toluidine | 0 | 0.5–2 | g/m² |
| | 5,5-Dimethyl-1,3-cyclohexanedione | 0 | 0.1–5 | g/m² |
| | 4-Aminoantipyrine HCl | 0.3–1.5 | 0.3–1.5 | g/m² |
| | Peroxidase | 20,000–30,000 | 20,000–30,000 | U/m² |
| | Glucose oxidase | 20,000–30,000 | 20,000–30,000 | U/m² |
| | Poly(ethylene terephthalate) Support | | | |

Controls A and B are similar to the elements described in Example 4 of U.S. Pat. No. 4,258,001 and in Example 2 of Japanese Patent Publication No. 57(1982)-101760, both noted hereinabove.

Each of several samples of these elements was spotted with 10 μL samples of undiluted whole blood containing varied amounts of glucose (60–650 mg/dL). Each element sample was incubated at room temperature for up to 5 minutes, and reflectance density readings were taken at 565 nm at various times within the incubation period using a conventional spectrophotometer.

Figure 2:
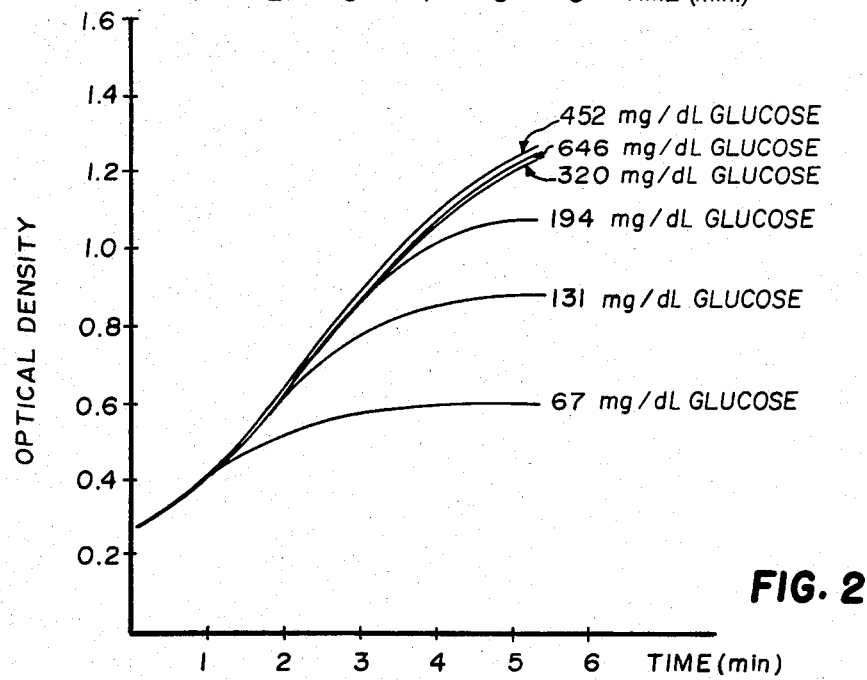

The results of the spectrophotometric readings are provided in FIGS. 2 and 3 for Control elements A and B, respectively. The results in FIGS. 2 and 3 indicate that the assay with Controls A and B are considerably slower than the assay of this invention, particularly at the higher glucose concentrations. The response curves show that an end point has not been reached even after 5 minutes. The results also indicate that, at the higher glucose concentrations, there is very poor discrimination between concentration levels.

EXAMPLE 2

Glucose Assay of this Invention Using Toluidine Coupler and Comparison with Prior Art Assay This is a comparative example similar to Example 1 except that a toluidine coupler was used in place of 8-anilino-1-naphthalenesulfonic acid.

An element was prepared according to this invention like that described in Example 1 except that from 0.5 to 5 g/m² of N-ethyl-N-2-sulfoethyl-m-toluidine was used as the coupler compound in place of 8-anilino-1-naphthalenesulfonic acid.

A Control element C was prepared similarly except that it included a radiation blocking/filter layer interposed between the reagent/spreading and registration layers. This additional layer was constructed like that for Controls A and B of Example 1. Control C is representative of the teaching of U.S. Pat. No. 4,042,335 (noted hereinabove).

Figure 5:
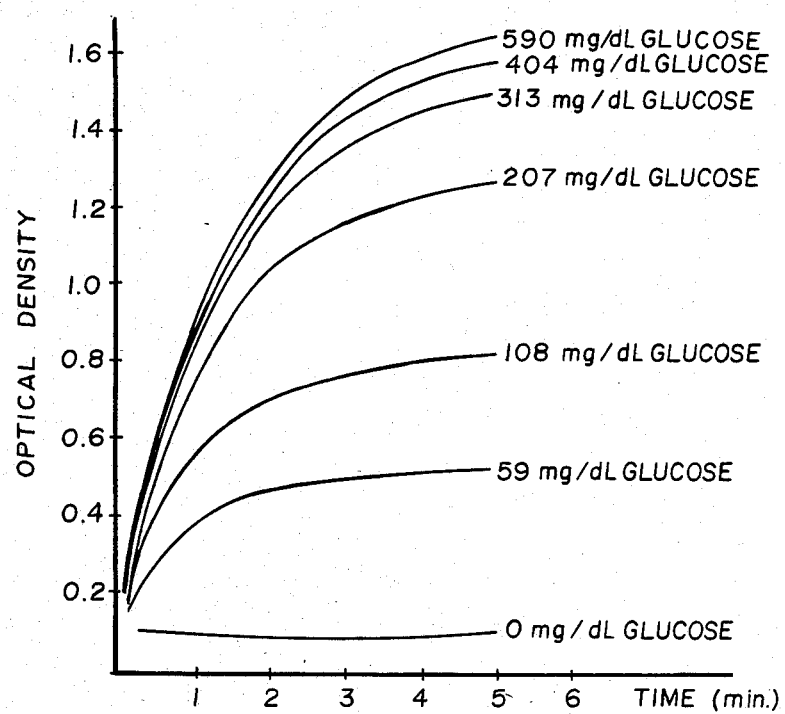
FIG. 5 is a graphical plot similar to FIG. 4 except that the glucose assay was carried out according to the teaching of the prior art.

Each of several samples of each element was spotted with 10 μL samples of undiluted whole blood containing varied amounts of glucose (0–590 mg/dL) and evaluated as the element samples were evaluated in Example 1. The element of this invention was evaluated at 660 nm to avoid hemoglobin interference, while Control C was evaluated at 565 nm since the radiation blocking/filter layer blocked out the hemoglobin interference. The dye released using the toluidine coupler can be spectrophotometrically detected at either wavelength although the λmax is closer to 565 nm. The results of the spectrophotometric readings are provided in FIGS. 4 and 5 for the invention element and Control C element, respectively.

These results indicate that the assay of this invention provides a more rapid assay than the Control C assay. The response curves for Control C are still rising after 5 minutes, particularly at the higher glucose concentrations whereas the invention response curves flatten out very quickly (less than 3 minutes). Also, there is poor discrimination with the Control C element especially at the higher glucose concentration levels.

EXAMPLE 3

Cholesterol Assay

An analytical element for the quantitative determination of cholesterol in whole blood was prepared in the following manner. On a poly(ethylene terephthalate) film support were coated, in order, a registration layer and a reagent/spreading layer having the component materials listed below.

| Reagent/Spreading Layer | |
|---|---|
| Particulate structure composed of: | |
| 40–60μ poly(vinyltoluene-co-p-t-butylstyrene-co-methacrylic acid) [61:37:2 weight ratio] beads, and | 100–300 g/m² |
| poly(n-butyl acrylate-co-styrene-co-2-acrylamido-2-methylpropane sulfonic acid) [70:20:10 weight ratio] adhesive | 2–10 g/m² |
| Triton X-100 ™ surfactant | 0.5–5 g/m² |
| Xanthan gum thickener | 0.05–0.5 g/m² |
| 5,5-Dimethyl-1,3-cyclohexanedione | 0.1–0.5 g/m² |
| 6-Amino-4,5-dihydroxy-2-methylpyrimidine | 0.5–10 g/m² |
| Potassium phosphate buffer (pH 6.25) | 0.5–10 g/m² |
| 4-Aminoantipyrine | 0.3–1.5 g/m² |
| N—ethyl-N—2-sulfoethyl-m-toluidine | 0.5–2 g/m² |
| Peroxidase | 20,000–30,000 U/m² |
| Cholesterol oxidase | 1,000–4,000 U/m² |
| Cholesterol ester hydrolase | 100–1,000 U/m² |
| Registration Layer | |
| Gelatin | 5–20 g/m² |
| Bis(vinylsulfonylmethyl)ether hardener | 0.01–1 g/m² |
| Potassium phosphate buffer | 0.5–10 g/m² |
| Triton X-100 ™ surfactant | 0.5–2 g/m² |
| Poly(ethylene terephthalate) Support | |

Figure 6:
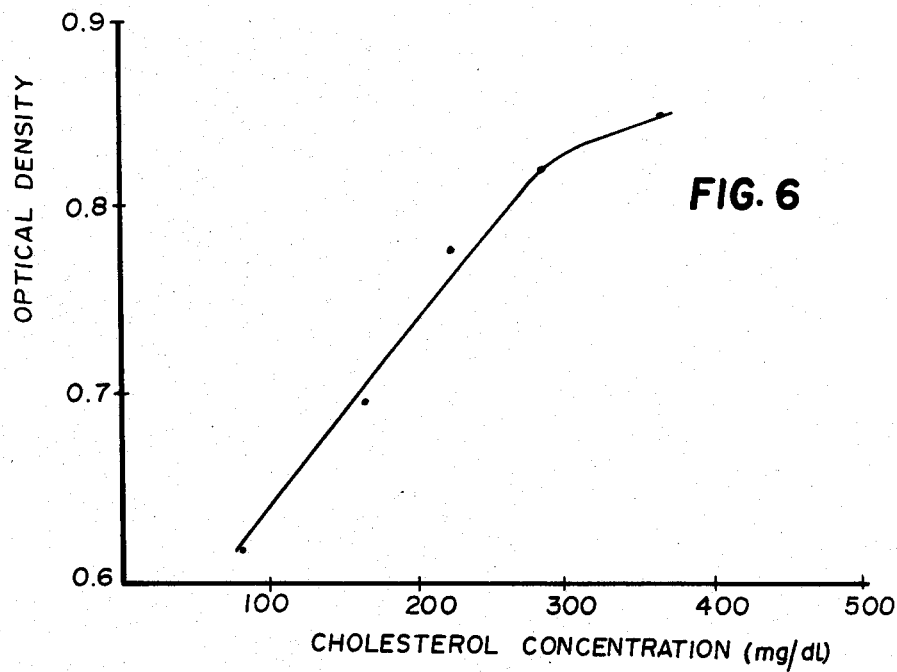
FIG. 6 is a graphical plot of optical density (Dr) measured at 630 nm vs. cholesterol concentration (mg/dL) for assays of undiluted whole blood samples containing various amounts of cholesterol determined according to this invention.

Each of several samples of this analytical element was spotted with a 10 μL sample of undiluted whole blood containing varied amounts of cholesterol (166, 226, 287 and 369 mg/L). Each element sample was incubated at 37° C. for up to 5 minutes, and reflectance density readings were taken at 630 nm at the end of the incubation period for each cholesterol concentration. The observed density readings were plotted as a function of concentration to give the calibration curve shown in FIG. 6.

The invention has been described in detail with particular reference to preferred embodiments thereof, but it will be understood that variations and modifications can be effected within the spirit and scope of the invention.

I claim:

1. A method for the determination of an analyte other than hemoglobin in whole blood comprising the steps of:
   (A) physically contacting a sample of whole blood containing an analyte other than hemoglobin and a multizone element, said element consisting essentially of support having thereon, in order and in fluid contact, a registration zone and a reagent/spreading zone,
   provided said element does not contain a radiation-blocking zone,
   said reagent/spreading zone having a void volume and average pore size effective to accommodate whole blood, an containing an interactive composition capable of providing, upon interaction with said analyte, a dye which can be spectrophotometrically detected at a wavelength greater than about 600 nm; and
   (B) detecting said dye at a wavelength greater than about 600 nm.

2. The method of claim 1 wherein said reagent/spreading zone comprises a particulate structure comprising a plurality of particles non-swellable in and impermeable to whole blood, said particles having a particle size of from about 1 to about 200 microns and being bonded together on surface areas of adjacent particles where said adjacent particles are in closest proximity to form a coherent, three-dimensional lattice which is non-swellable in whole blood.

3. The method of claim 2 wherein said particles are chemically bonded through reactive groups at the points of particle contact which reactive groups are incorporated in said particles.

4. The method of claim 2 wherein said particles are bonded with an adhesive material.

5. The method of claim 1 wherein said reagent/spreading zone comprises a fibrous material.

6. The method of claim 1 wherein said interactive composition comprises a substance having peroxidative activity.

7. The method of claim 1 wherein said void volume is from about 40 to about 60 percent and said average pore size is at least 5 microns.

8. A method for the determination of an analyte other than hemoglobin in whole blood comprising the steps of:
(A) physically contacting a sample of whole blood containing an analyte other than hemoglobin and a multizone element, said element consisting of a support having thereon, in order and in fluid contact, a registration zone, a subbing zone and a reagent/spreading zone,
said reagent/spreading zone having a void volume and average pore size effective to accommodate whole blood, and containing an interactive composition capable of providing, upon interaction with said analyte, a dye which can be spectrophotometrically detected at a wavelength greater than about 600 nm; and
(B) quantitatively detecting said dye at a wavelength greater than about 600 nm.

9. A method for the determination of an analyte other than hemoglobin in whole blood comprising the steps of:
(A) physically contacting a sample of whole blood containing an analyte other than hemoglobin and a multizone element, said element consisting essentially of a support having thereon, in order and in fluid contact, a registration zone and a reagent/spreading zone,
provided said element does not contain a radiation-blocking zone,
said reagent/spreading zone containing an interactive composition capable of providing, upon interaction with said analyte, a dye which can be spectrophotometrically detected at a wavelength greater than about 600 nm,
said reagent/spreading zone also comprising a particulate structure having a void volume of from about 40 to about 60 percent and an average pore size of at least 5 microns, said particulate structure comprising:
(i) a plurality of heat-stable, organopolymeric particles non-swellable in and impermeable to whole blood, said particles having a particle size of from about 1 to about 200 microns, and
(ii) an adhesive, in an amount less than about 10 percent by weight of said particles, comprising an organic polymer different from that of said particles and insoluble in whole blood;
substantially all of said adhesive being concentrated on surface areas of adjacent particles where said adjacent particles are in closest proximity, and bonding said particles together with said adhesive into a coherent, three-dimensional lattice which is non-swellable in whole blood; and
(B) quantitatively detecting said dye at a wavelength greater than about 600 nm.

10. The method of claim 9 wherein said analyte is glucose.

11. The method of claim 9 wherein said analyte is cholesterol.

12. A method for the determination of glucose in whole blood comprising the steps of:

(A) physically contacting a sample of whole blood containing glucose and a multilayer element, said element consisting essentially of support having thereon, in order and in fluid contact, a registration layer and a reagent/spreading layer,
provided said element does not contain a radiation-blocking layer,
said reagent/spreading layer having a void volume and average pore size effective to accommodate whole blood, and containing a composition comprising glucose oxidase, a substance having peroxidative activity, an amino-antipyrine and a color-forming coupler which, upon the interaction of said composition with glucose, provides a dye which can be spectrophotometrically detected at a wavelength greater than about 600 nm; and
(B) quantitatively detecting said dye at a wavelength greater than about 600 nm.

13. The method of claim 12 wherein said peroxidative substance is peroxidase, and said aminoantipyrine is 4-aminoantipyrine.

14. The method of claim 12 carried out at a pH of from about 4 to about 7.

15. The method of claim 12 wherein said color-forming coupler is a toluidine compound or a substituted aniline compound.

16. A multizone element for the determination of an analyte other than hemoglobin in whole blood consisting essentially of a support having thereon, in order and in fluid contact, a registration zone and a reagent/spreading zone,
provided said element does not contain a radiation-blocking zone,
said reagent/spreading zone having a void volume and average pore size effective to accommodate whole blood containing an anlyte other than hemoglobin and containing an interactive composition for said analyte,
said interactive composition comprising a substance having peroxidative activity, and capable of providing, upon interaction with said analyte, a dye which can be spectrophotometrically detected at a wavelength greater than about 600 nm.

17. The element of claim 16 wherein said void volume of said reagent/spreading layer is from about 25 to about 80 percent and said average pore size is at least 5 microns.

18. The element of claim 16 wherein said analyte is glucose.

19. The element of claim 16 wherein said analyte is cholesterol.

20. The element of claim 16 wherein said reagent/spreading zone comprises a fibrous material.

21. A multizone element for the determination of an analyte other than hemoglobin in whole blood consisting essentially of a support having thereon, in order and in fluid contact, a registration zone and a reagent/spreading zone,
provided said element does not container a radiation-blocking zone,
said reagent/spreading zone comprising a particulate structure having a void volume and average pore size effective to accommodate whole blood containing an analyte other than hemoglobin,
said particulate structure comprising a plurality of particles non-swellable in and impermeable to whole blood, said particles having a particle size of from about 1 to about 200 microns and being bonded together on surface areas of adjacent particles where said adjacent particles are in closest proximity to form a coherent, three-dimensional lattice which is non-swellable in whole blood, said reagent/spreading zone containing an interactive composition necessary for said determination, said interactive composition comprising a substance having peroxidative activity, and capable of providing, upon interaction with said analyte, a dye which can be spectrophotometrically detected at a wavelength greater than about 600 nm.

22. The element of claim 21 wherein said particles are chemically bonded through reactive groups at the points of particle contact which reactive groups are incorporated in said particles.

23. The element of claim 21 wherein said particles are bonded together with an adhesive material.

24. A multizone element for the determination of an analyte other than hemoglobin in whole blood consisting essentially of a support having thereon, in order and in fluid contact, a registration zone and a reagent/spreading zone, provided said element does not contain a radiation-blocking zone, said reagent/spreading zone also comprising a particulate structure having a void volume of from about 40 to about 60 percent and an average pore size of at least from about 15 to about 65 microns, said particulate structure comprising:

(i) a plurality of heat-stable, organopolymeric particles non-swellable in and impermeable to whole blood containing an analyte other than hemoglobin, said particles having a particle size of from about 1 to about 200 microns, and (ii) an adhesive, in an amount less than about 10 percent by weight of said particles, comprising an organic polymer different from that of said particles and insoluble in whole blood;

substantially all of said adhesive being concentrated on surface areas of adjacent particles where said adjacent particles are in closest proximity, and bonding said particles together with said adhesive into a coherent, three-dimensional lattice which is non-swellable in whole blood, said reagent/spreading zone containing an interactive composition comprising a substance having peroxidative activity, and capable of providing, upon interaction with said analyte, a dye which can be spectrophotometrically detected at a wavelength greater than about 600 nm.

25. The element of claim 24 wherein said particles comprise an addition polymer formed from one or more of the following ethylenically unsaturated polymerizable monomers:

(a) up to 100 weight percent of an amino-substituent-free vinyl carbocyclic aromatic;

(b) up to about 25 weight percent of an acrylic acid ester;

(c) up to 100 weight percent of a methacrylic acid ester;

(d) up to about 30 weight percent of an ethyleically unsaturated carboxylic acid;

(e) up to about 75 weight percent of an ethylenically unsaturated nitrile;

(f) up to about 20 weight percent of an amino-substituted vinyl carbocyclic aromatic;

(g) up to about 20 weight percent of an ethylenically unsaturated crosslinkable monomer;

(h) up to about 20 weight percent of a tertiary aminoalkyl acrylate or methacrylate;

(i) up to 100 weight percent of a N-heterocyclic vinyl monomer; and (j) up to about 20 weight percent of an acrylamide or methacrylamide, and said adhesive comprises an addition polymer formed from a blend of ethylenically unsaturated polymerizable monomers selected from the following group:

A. a blend containing from about 1 to about 35 weight percent of one or more amino-substituent-free vinyl carbocyclic aromatics and from about 65 to about 99 weight percent of one or more alkyl acrylates or methacrylates;

B. a blend containing from about 20 to about 95 weight percent of one or more amino-substituent-free vinyl carbocyclic aromatics, acrylic or methacrylic acid esters and ethylenically unsaturated polymerizable crosslinkable monomers, and from about 5 to about 80 weight percent of one or more ethylenically unsaturated polymerizable monomers having an active hydrogen or salts thereof; and C. a blend containing from about 15 to 100 weight percent of one or more ethylenically unsaturated monomers selected from the group consisting of 1-vinylimidazole, vinylbenzyl alcohol, ethyl acrylate or an acrylamide or methacrylamide, and up to 85 weight percent of one or more ethylenically unsaturated polymerizable crosslinkable monomers.

26. A multilayer element for the determination of glucose in whole blood consisting essentially of a support having thereon, in order and in fluid contact, a registration layer and a reagent/spreading layer, provided said element does not contain a radiation-blocking layer, said spreading/reagent layer having a void volume and average pore size effective to accommodate whole blood containing glucose, and containing an interactive composition comprising glucose oxidase, a substance having peroxidative activity, an aminoantipyrine and a color-forming coupler which, upon the interaction of said composition with glucose, provides a dye which can be spectrophotometrically detected at a wavelength greater than about 600 nm.

27. The element of claim 26 wherein said interactive composition comprises peroxidase, 4-aminoantipyrine and a buffer which maintains a pH of from about 4 to about 7.

28. The element of claim 26 wherein said color-forming coupler is a toluidine compound or a substituted aniline compound.

29. The element of claim 28 wherein said interactive composition comprises glucose oxidase, peroxidase, 4-aminoantipyrine, 3,3-dimethylglutaric acid and 8-anilino-1-naphthalenesulfonic acid; and said reagent/spreading layer comprises a particulate structure comprising (i) a plurality of poly(vinyltoluene-co-p-t-butylstyrene-co-methacrylic acid) particles having a substantially uniform particle size of from about 40 to about 60 microns; and (ii) an adhesive, in an amount less than about 10 percent by weight of said particles, comprising poly(n- butyl acrylate-co-styrene-co-2-acrylamido-2-methylpropane sulfonic acid).

30. A multizone element for the determination of an analyte other than hemoglobin in whole blood consisting of a support having thereon, in order and in fluid contact, a registration zone, a subbing zone and a reagent/spreading zone, said reagent/spreading zone having a void volume and average pore size effective to accommodate whole blood containing an analyte other than hemoglobin, and containing an interactive composition for said analyte, said interactive composition comprising a substance having peroxidative activity, and capable of providing, upon interaction with said analyte, a dye which can be spectro-photometrically detected at a wavelength greater than about 600 nm.

* * * * *